United States Patent [19]

Chu

[11] Patent Number: 5,258,495
[45] Date of Patent: Nov. 2, 1993

[54] PROCESS FOR MAKING VANCOMYCIN HCl

[75] Inventor: Alexander H. T. Chu, Buffalo Grove, Ill.

[73] Assignee: Abbott Laboratories, Abbott Park, Ill.

[21] Appl. No.: 875,555

[22] Filed: Apr. 27, 1992

Related U.S. Application Data

[63] Continuation-in-part of Ser. No. 550,427, Jul. 10, 1990, abandoned.

[51] Int. Cl.$^5$ ............................ C07K 1/14; C07K 9/00
[52] U.S. Cl. .................................. 530/344; 530/317; 530/322
[58] Field of Search ................ 530/317, 322, 323, 344

[56] References Cited

U.S. PATENT DOCUMENTS

| | | | |
|---|---|---|---|
| 3,067,099 | 12/1962 | McCormick et al. | 424/115 |
| 4,440,753 | 4/1984 | McCormick et al. | 424/124 |
| 4,667,024 | 5/1987 | Sitrin et al. | 536/16.9 |
| 4,845,194 | 7/1989 | Glass et al. | 530/344 |

FOREIGN PATENT DOCUMENTS

| | | |
|---|---|---|
| 0145484 | 6/1985 | European Pat. Off. |
| 0241758 | 10/1987 | European Pat. Off. |
| 0262941 | 4/1988 | European Pat. Off. |
| 0294990 | 12/1988 | European Pat. Off. |
| 0303021 | 2/1989 | European Pat. Off. |
| 0323150 | 7/1989 | European Pat. Off. |
| 2151234B | 7/1985 | United Kingdom. |

*Primary Examiner*—Y. Christina Chan
*Attorney, Agent, or Firm*—Andreas M. Danckers

[57] ABSTRACT

A process for the manufacture of vancomycin.HCl which does not require preparation of a phosphate intermediate. The process consists of loading a vancomycin onto a suitable adsorbent and eluting the vancomycin solution therefrom with an ammonium solvent followed by loading the vancomycin solution onto a suitable adsorbent and eluting the purified, vancomycin solution therefrom with a solvent of alcohol and acid. The purified vancomycin is then crystallized from the solution by combining the solution with a sufficient amount of NH$_4$Cl to provide a pH of about 2.0 to about 3.5. The crystals are then dissolved in solution. The dissolved solution is combined with acid and the vancomycin recrystallizes from the solution.

8 Claims, 1 Drawing Sheet

PROCESS FOR MAKING VANCOMYCIN HCl

This application is a continuation-in-part of U.S. application Ser. No. 07/550,427, filed Jul. 10, 1990, now abandoned.

TECHNICAL FIELD

The present invention relates to a process for the manufacture of vancomycin.HCl.

BACKGROUND OF THE INVENTION

Vancomycin is used to treat serious infections of methicillin-resistant staphylococci. Vancomycin is produced by cultivating the bacteria *S. orientalis* in a nutrient culture media.

The vancomycin broth is filtered and added to a column that contains an adsorption resin that decolorizes and desalts the vancomycin. The resin is washed, and the vancomycin eluted with a solvent of low pH, followed by decolorization with carbon.

The vancomycin eluant is then further purified using a single recrystallization step at low pH. The crystallized vancomycin is combined with a strong acid such as hydrochloric acid (HCl) and precipitated in an organic solvent such as acetone to form vancomycin HCl. This process for the manufacture and purification of vancomycin.HCl is disclosed in U.S. Pat. No. 3,067,099 to McCormick et al.

In another example of a prior art process for the manufacture of vancomycin.HCl, a solvent of 0.1% phosphoric acid ($H_3PO_4$) in a solution of 10% isopropyl alcohol (IPA) is used to elute purified vancomycin from the adsorption column. The vancomycin eluant is then concentrated using reverse osmosis or vacuum evaporation. An aqueous solution that is approximately 60 g/l of potassium phosphate ($KH_2PO_4$) is added to the concentrated vancomycin solution. The $KH_2PO_4$ causes the vancomycin to crystallize from the solution. The resulting slurry is centrifuged to remove the excess liquid. The vancomycin crystals obtained from centrifugation of the slurry are reslurried in sodium hydroxide (NaOH) to a pH of approximately 4.5 followed by treatment with $KH_2PO_4$ to a pH of approximately 2.0. Vancomycin again crystallizes from the solution. The resulting slurry is centrifuged to separate the crystals from the liquid. The resultant solid is dissolved in water and the mixture is eluted in an ion exchange column to prepare vancomycin hydrochloride.

European Patent Application, Publication No. 0323150 to Catt et al. discloses an alternate method to precipitate vancomycin in a base solution with a pH of 7.8 to 9.0. At pH's above about 9.0, the base crystallization disclosed in Catt et al. is unsatisfactory because reduced yields and discolored products result; pH's of 8.0 to 8.5 are preferred for the crystallization disclosed by this reference.

SUMMARY OF THE INVENTION

The invention herein is a process for the manufacture of vancomycin.HCl using ammonium chloride ($NH_4Cl$) crystallization at a pH of about 2.0 to about 3.5. Vancomycin is concentrated and purified by elution with a base solvent through a column with a suitable adsorbent therein followed by elution through a second column with another suitable adsorbent therein which decolorizes and desalts the vancomycin. The solvent used in the second column is an acid/alcohol solution, the alcohol being an approximately 10% solution of ethanol or isopropyl alcohol. Ammonium chloride is added to the vancomycin eluant in an amount sufficient to impart to the resulting solution a pH of approximately 2.0 to 3.5. The vancomycin crystallizes and precipitates from the solution. The crystals are then separated from the solution.

The crystals are redissolved at a pH above 9.0 and a sufficient amount of ammonium chloride or hydrochloric acid is added to the dissolved solution to impart a pH of about 2.0 to about 3.5 to the solution. Recrystallized vancomycin results. The resulting crystals are then separated from the solution and dried.

The present process has distinct advantages over the prior art. First, the vancomycin purity from this process ($90 \pm 1\%$) is at least 2-3% higher than those obtained by other processes. The purity is increased without additional chromatographic, extraction, or complex formation steps for further purification. Secondly, some time-consuming and expensive conversion steps using ion-exchange resins to obtain the desired hydrochloride salt are totally eliminated.

DETAILED DESCRIPTION OF THE PREFERRED EMBODIMENTS

Figure 1:
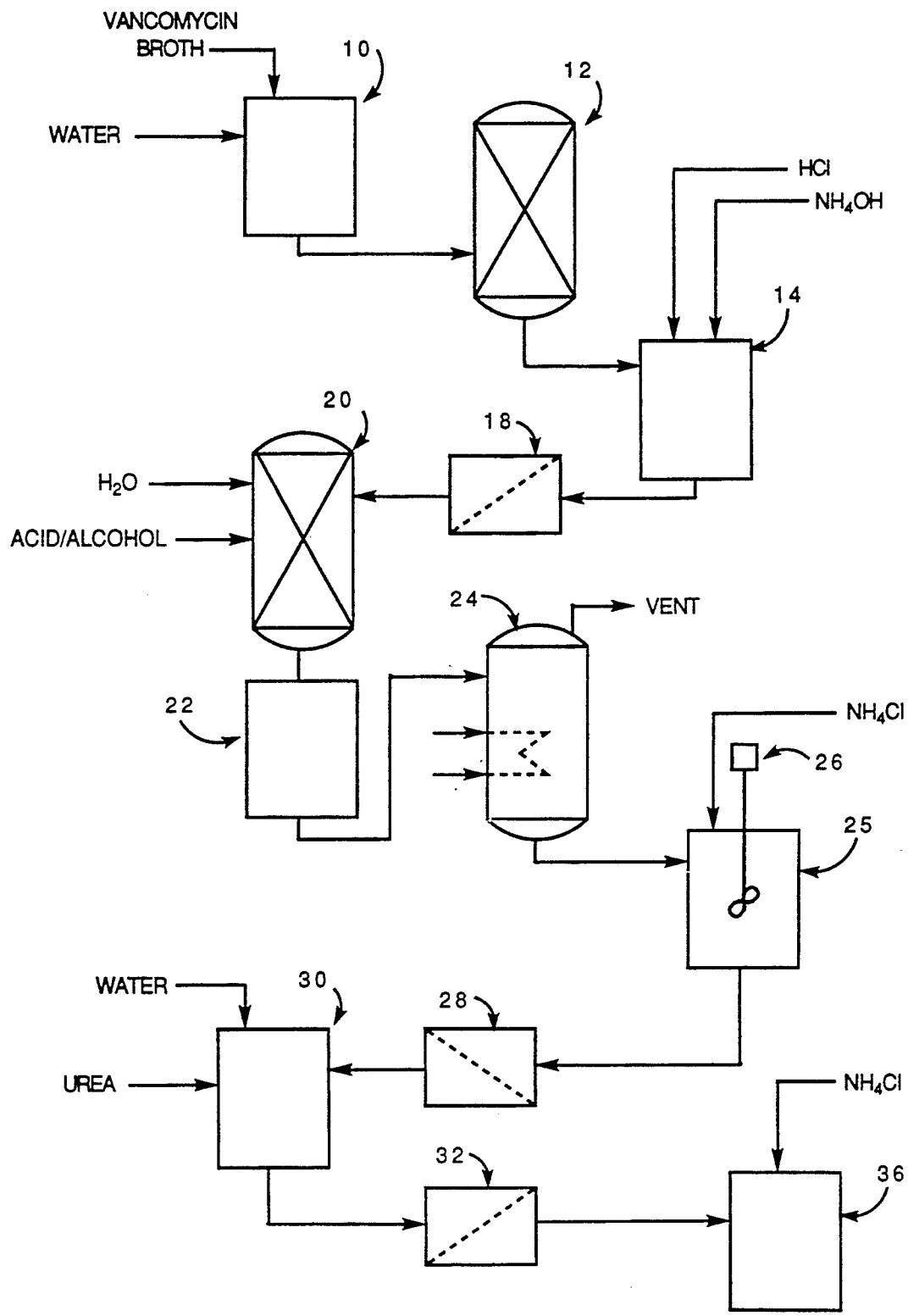
FIG. 1 is a flow diagram of an embodiment of the process disclosed herein.

Vancomycin typically is prepared in a fermentor. Vancomycin is then separated for activity and purified. Typically, the desired vancomycin is separated from other strains of vancomycin and other impurities by elution of "raw" vancomycin through a column with an adsorbent therein. The preferred active strain of vancomycin is vancomycin B. For purposes of this disclosure, adsorbents that are selective for vancomycin B such as DOWEX 50 WX2, a cation-exchange resin available from Dow Chemical, and AMBERLITE XAD-16, a non-functional resin available from Rohm & Haas, were utilized to separate other strains of vancomycin and impurities from the vancomycin B.

Elutions are performed in fractions. Each fraction is analyzed to determine the concentration and quantity of vancomycin B therein. In this way the fractions with the greatest concentration of the desired strain of vancomycin can be combined to optimize the yield from the process. The fractions, for convenience, are expressed in the number of bed or column volumes they represent. The purity of the vancomycin varies from fraction to fraction and depends on a number of factors such as the solvent used to elute the vancomycin from the column and the fermentation medium.

Referring now to the scheme shown in FIG. 1, vancomycin enriched Dowex 50 resin is obtained and rinsed with water in a screened sanitary tank 10. The resin is loaded onto a six-inch column 12 and eluted with one bed volume of 0.5N $NH_4OH$ and five to seven bed volumes of 0.25N $NH_4OH$. The resin is eluted and the fractions are collected, analyzed for the presence of the desired strain of vancomycin and combined in sanitary tank 14. The pH of the fractions is adjusted by adding hydrochloric acid to tank 14 in an amount sufficient to lower the pH to 3.5. The fractions are pooled by using thin layer chromatography to determine which fractions have acceptable amounts of the desired vancomycin B strain therein.

The pH of the combined eluates is increased to about 7 to about 7.5 by adding a sufficient amount of NH₄OH. The solution is mixed with filter aid and then filtered through a 0.1μ PALL depth filter 18 to remove hazy precipitates. The filtered solution is then loaded onto a six-inch XAD-16 resin column 20 at a loading capacity of approximately 30 g/l. The column 20 is washed with water. The enriched XAD-16 resin is then eluted with six to seven bed volumes of a solution of 0.1% HCl in an aqueous solution that is 10% isopropyl alcohol. Fractions are collected and pooled in sanitary vessel 22 based on the activity detected by thin layer chromatography.

The mixture is then concentrated in a thin film evaporator 24 to remove the alcohol. The solution is concentrated to 250 grams of vancomycin per liter of solution. The concentrated solution is placed in sanitary tank 25.

The concentrated vancomycin solution is combined with 30 to 60 g/l of ammonium chloride (NH₄Cl), and a solution pH of about 2.0 to 3.5 results. A thick gel forms immediately when a vancomycin concentration of about 200 to about 250 g/l is used, while a very heavy slurry forms when about a 100 to about 150 g/l concentration of vancomycin is used. Also, when a higher solution pH is maintained the gel appears thicker. The mixture is stirred continuously using mixer 26 to keep the gel dispersed in solution.

Crystals form over a 24–48 hour period. The slurry is vacuum filtered in filter 28. The solids are placed in sanitary tank 30. The crystals are reslurried by adding water to the tank 30.

The vancomycin is recrystallized by first dissolving vancomycin crystals in urea that is added to tank 30. A high concentration of urea (2–6M) is used to dissolve the vancomycin crystals and to release color bodies which are physically entrapped in the vancomycin molecules. After the crystals are dissolved in tank 30, the solution is diafiltered using reverse osmosis (MILLIPORE NF40) with 400 molecular weight cut off (MWCO) or ultrafiltration (1000 MWCO) membranes in module 32. The module 32 diafilters urea and residual salts from the dissolved solution. The filtrate is a clear concentrate which is placed in sanitary vessel 36. NH₄Cl is then added to the concentrated, filtered solution in sanitary tank 36.

In an alternate method for recrystallizing vancomycin using this process, ammonium hydroxide (NH₄OH) is used to dissolve the crystals obtained from the first crystallization step. The NH₄OH is added to the solution in tank 30 in an amount sufficient to raise the pH to above about 10.0±0.5. The vancomycin activity is stable (less than 2% degradation) at a pH of 10.5 for about 2 hours at room temperature. The solution pH is then reduced to about 2.0 to 3.5 by adding a sufficient amount of hydrochloric acid (HCl). After adding the HCl, the solution becomes immediately cloudy. If the pH is reduced below 9.0, a gel forms when the pH reaches 7.5 which follows as more HCl is added. As still more HCl is added, the gel softens to a slurry. Crystals precipitate from the solution overnight at pH 2.0–3.5.

EXAMPLE I

Crystals made according to the previously described process were washed or reslurried by adding a solution that was 0 to 60 g/l NH₄Cl in water. The higher NH₄Cl concentrations reduced vancomycin loss in the mother liquor but did not remove color as effectively. The solids were then dried under vacuum under 50° C. (90° F.) and the dried solid was milled for analysis.

Five batches of vancomycin were made according to the above-described process. The products were analyzed for purity, yield, pH and a variety of other properties to determine their acceptability. Table I is a summary of these test results.

TABLE I

Product Quality[1] and Yield from NH₄Cl Crystallization at pH 3.0 ± 0.5

| Sample | 1 | 2 | 3 | 4 | 5 |
|---|---|---|---|---|---|
| Purity (HPLC[2]) | 90.0% | 86.3 | 89.4 | 91.4 | 90.8 |
| Major Impurity | 2.4% | 3.1 | 2.9 | 2.2 | 2.3 |
| APHA[3] Color | 300 | 300 | 300 | 300 | 300 |
| pH (2.8–4.2) | 3.6 | 3.6 | 3.3 | 3.2 | 3.5 |
| % Moisture | 1.9% | 2.8 | 0.8 | 2.8 | 4.3 |
| % ROI (ash)[5] | 0.0% | 0.0 | 0.0 | — | — |
| Heavy metal (Pb) | <0.002% | <30 ppm | <30 ppm | <30 ppm | <30 ppm |
| Biopotency (μg/mg) | 996 | 1046 | 1072 | 973 | 1006 |
| Step yield: | | | | | |
| Dowex resin - >concn. | 95% | ~99% | 97% | 98% | 96% |
| Crystallization | 90% | 90% | 92% | 72% | 89% |
| Recrystallization | 95% | 90% | 83% | 96% | 82% |
| Overall Yield[4] | | | | | |
| by activity | 73% | 70% | 67% | 61% | 63% |
| by weight | 81% | 81% | 75% | 67% | 69% |

[1]All products are in powder form and meet infrared identification requirements.
[2]High Pressure Liquid Chromatography
[3]APHA: American Public Health Association
[4]Assume 90% beer adsorption
[5]Residue of ignition The high pressure liquid chromatography (HPLC) purities of the final products were between 86 and 92% and the APHA color readings were 300 which is acceptable. Residual phosphate and acetate levels were essentially nondetectable and the ashes (ROI) were less than 0.1% where tested. Anhydrous biopotencies were all approximately 1000 micro grams per milligram which is acceptable.

The examples herein illustrate yields of from 65% to 81% by weight assuming a 90% yield in the step from the harvest from production to the eluate from the DOWEX 50 resin (the first elution).

EXAMPLE II

Effect of pH During NH₄Cl Crystallization on Product Purity and Color

A suitable process for the production of vancomycinHCl must adequately remove color impurities from the final product. Although color removal accomplished by eluting vancomycin with a solvent in AMBERLITE XAD-16, a macroreticular resin, residual color that remains in the vancomycin must be removed during the crystallization and recrystallization steps. Table II illustrates the effect of pH on color removal during crystallization. The table illustrates that improved color removal is achieved at a pH of 2.06 as opposed to 2.97, but at the expense of yield.

TABLE II

Effect of Varying pH During NH4Cl Crystallization on Product Purity and Color

| Sample[1] | 6 | 7 |
|---|---|---|
| Initial Conc. | 87.6 g/l | 87.6 g/l |
| pH | 2.06 | 2.97 |
| Product: | | |
| APHA color | 100 | 450 |
| pH | 2.29 | 3.30 |
| HPLC purity | 92.48% | 90.91% |
| Largest Single Impurity (LSI) | 1.31% | 2.19% |
| % Moisture | 0.91% | 3.54% |
| % Acetone | 1.7% | 0.0% |
| Crystallization Step Yield: | | |
| by activity | 66% | 75% |
| by weight | 71% | 83% |
| Mass Balance | 99% | 98% |

[1] Both samples meet the infrared identification standard.

EXAMPLE III

Effect of pH and Concentration on Product Quality and Yield

Table III illustrates that there is no appreciable difference in color removal if the NH4Cl crystallization occurs at a pH of 2.0 or 2.5, but that the initial concentration of vancomycin significantly effects the color of the product obtained from crystallizations at these pH's. Acceptable color removal is obtained when the initial vancomycin concentration is 112 g/l, regardless of whether the pH of the solution was 2.0 or 2.5. Unacceptable color removal is obtained at higher concentrations whether the pH was 2.0 or 2.5 although yield was somewhat improved at the higher concentrations.

TABLE III

Effect of Varying pH and Initial Concentration on Vancomycin.HCl Quality and Yield

| Sample | 8 | 9 | 10 | 11 |
|---|---|---|---|---|
| Initial conc. (g/l solid) | 112 | 112 | 225 | 225 |
| pH | 2.0 | 2.5 | 2.0 | 2.5 |
| NH4Cl (g/l) | 120 | 120 | 30 | 30 |
| Product: | | | | |
| HPLC purity | 91.74% | 91.67% | 91.54% | 91.28% |
| LSI | 2.04% | 2.04% | 2.01% | 2.07% |

TABLE III-continued

Effect of Varying pH and Initial Concentration on Vancomycin.HCl Quality and Yield

| Sample | 8 | 9 | 10 | 11 |
|---|---|---|---|---|
| APHA color | 300 | 300 | 400 | 350 |
| Crystallization recovery (by weight) | 64.5% | 76.9% | 75.7% | 85.8% |

The foregoing example are intended as illustrations only and are not intended to limit the invention in any way except in the spirit and scope of the appended claims.

We claim:

1. A process for the manufacture of crystallized vancomycin.HCl wherein vancomycin formed by fermentation is precipitated directly as a hydrochloride salt by adding a sufficient amount of ammonium chloride to vancomycin eluate to produce a solution with a pH of about 2.0 to about 3.5.

2. A process for the manufacture of vancomycin.HCl comprising:
   a) passing the raw vancomycin through a first adsorbent;
   b) passing the vancomycin eluate produced by step a) through a second adsorbent;
   c) adding an ammonium chloride solution to the product of step b) in an amount sufficient to produce a solution with a pH of about 2.0 to about 3.5;
   d) crystallizing vancomycin.HCl from the solution of step c);
   e) dissolving the vancomycin.HCl crystals from step d) in a base solution;
   f) adding to the dissolved solution of step e) an acid selected from the group consisting of ammonium chloride and hydrochloric acid;
   g) crystallizing vancomycin.HCl from the solution of step f); and
   h) separating the vancomycin.HCl crystals from the solution.

3. The process of claim 2 wherein the vancomycin is eluted through the first adsorbent with a base solvent.

4. The process of claim 2 further comprising concentrating the vancomycin solution from step b).

5. The process of claim 2 wherein the base solution is an aliquot of ammonium hydroxide in an amount sufficient to produce a pH of about 9.5–10.5 when combined with the vancomycin.HCl crystals.

6. The process of claim 5 wherein the acid in step f) is an aliquot of hydrochloric acid in an amount sufficient to impart a pH of about 2.0 to about 3.5 to the solution of step f).

7. The process of claim 2 wherein the base solution in step e) is a urea solution.

8. The process of claim 7 wherein the acid in step f) is an ammonium chloride solution.

* * * * *